United States Patent
Posner et al.

(12)
(10) Patent No.: US 6,193,948 B1
(45) Date of Patent: Feb. 27, 2001

(54) ANTIGEN RECOGNIZED BY PATIENTS WITH ANTIBODY ASSOCIATED PARANEOPLASTIC SENSORY NEURONOPATHY, DNA ENCODING SAME AND USES THEREOF

(75) Inventors: Jerome B. Posner; Henry M. Furneaux, both of New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/082,501

(22) Filed: May 21, 1998

Related U.S. Application Data

(60) Continuation of application No. 08/461,027, filed on Jun. 5, 1995, now Pat. No. 5,807,705, which is a division of application No. 08/210,732, filed on Mar. 18, 1994, now Pat. No. 5,603,934, which is a continuation of application No. 07/665,959, filed on Mar. 4, 1991, now abandoned.

(51) Int. Cl.$^7$ ............................ A61K 51/00; A61M 36/14
(52) U.S. Cl. .................... 424/1.49; 424/1.11; 424/185.1; 424/1.57; 435/69.3; 435/69.1
(58) Field of Search ................................ 424/1.11, 1.49, 424/1.65, 9.1, 9.3, 9.4, 9.5, 9.6, 9.7, 185.1, 1.57, 193.1; 435/69.3, 69.7, 320.1, 325, 252.3; 514/2, 12; 436/56, 57; 536/23.5

(56) References Cited

U.S. PATENT DOCUMENTS

| | | | | |
|---|---|---|---|---|
| 5,603,934 | * | 2/1997 | Posner et al. | ........... 424/185.1 |
| 5,807,705 | * | 9/1998 | Posner et al. | ............. 435/69.1 |

OTHER PUBLICATIONS

Brain, L. and Wilkinson, M. (1965) "Subacute cerebellar degeneration associated with neoplasms." *Brain* 88: 465–478.

Dalmau, J., et al. (1990) "Detection of the anti–Hu antibody in the serum of patients with small cell lung cancer–A quantitative Western blot analysis." *Ann. Neurol.* 27: 544–552.

Dalmau, J., et al. (1991) "Detection of the anti–Hu antibody in specific regions of the nervous system and tumor from patients with paraneoplastic encephalomyelitis/sensory neuronpathy." *Neurology* 41: 1757–1764.

Furneaux, H.M., et al. (1990) "Autoantibody synthesis in the central nervous system of patients with paraneoplastic syndromes." *Neurology* 40: 1085–1091.

Graus, F., et al. (1985) "Neuronal antinuclear antibody in sensory neuronopathy from lung cancer." *Neurology* 35: 538–543.

Graus, F., et al. (1987) "Neuronal antinuclear antibody (anti–Hu) in paraneoplastic encephalomyelitis stimulating acute polyneuritis." *Acta Neurol. Scand.* 75: 249–252.

Posner, J.B. and Furneaux, H.M. (1990) "Paraneoplastic Syndromes." *Immunologic Mechanisms in Neurologic and Psychiatric Disease* (ed. B.H. Waksman, Raven Press, Ltd.) 187–219.

Szabo, A., et al. (1991) "HuD, a paraneoplastic encephalomeylitis antigen, contains RNA–binding domains and is homologous to Elav and Sex–Lethal." *Cell* 67: 325–333.

\* cited by examiner

*Primary Examiner*—Jose' G. Dees
*Assistant Examiner*—Dameron Jones
(74) *Attorney, Agent, or Firm*—Hamilton, Brook, Smith & Reynolds, P.C.

(57) ABSTRACT

An isolated nucleic acid sequence encoding Hu paraneoplastic antigenic polypeptide is provided by this invention. This invention also provides a purified Hu antigenic polypeptide and compositions containing the purified Hu antigenic polypeptide. Further provided by this invention is a monoclonal antibody directed to an epitope on the Hu paraneoplastic antigenic polypeptide. Compositions containing this monoclonal antibody also are provided by this invention. This invention also provides methods of diagnosis and treatment using the compositions described hereinabove.

11 Claims, 7 Drawing Sheets

FIGURE 4A

| | | | | |
|---|---|---|---|---|
| CCAATAGTAG | TCATTTTAAA | TATATATTCT | GAAATCTTTG | CAAATTTTAA | CAGAAGAGTC | 60
| GAAGCTCTGC | GAGACCCAAT | ATTGCCAAT | AAGAATGGTT | ATGATAATTA | GCACCATGGA | 120
| GCCTCAGGTG | TCAAATGGTC | CGACATCCAA | TACAAGCAAT | GGACCCTCCA | GCAACAACAG | 180
| AAACTGTCCT | TCTCCCATGC | AAACAGGGGC | AACCACAGAT | GACAGCAAAA | CCAACCTCAT | 240
| CGTCAACTAT | TTACCCCAGA | ATATGACCCA | AGAAGAATTC | AGGAGTCTCT | TCGGGAGCAT | 300
| TGGTGAAATA | GAATCCTGCA | AACTTGTGAG | AGACAAAATT | ACAGGACAGA | GTTTAGGGTA | 360
| TGGATTTGTT | AACTATATTG | ATCCAAAGGA | TGCAGAGAAA | GCCATCAACA | CTTTAAATGG | 420
| ACTCAGACTC | CAGAGACGGT | CTCATATGCC | CGTCCGAGCT | CTGCCTCAAT | 480
| CAGGGATGCT | AACCTCTATG | TTAGCGGCCT | TCCCAAAACC | ATGACCCAGA | AGGAACTGGA | 540
| GCAACTTTTC | TCGCAATACG | GCCGTATCAT | CACCTCACGA | ATCCTGGTTG | ATCAAGTCAC | 600
| AGGAGTGTCC | AGAGGGGTGG | GATTCATCCG | CTTTGATAAG | AGGATTGAGG | CAGAAGAAGC | 660
| CATCAAAGGG | CTGAATGGCC | AGAAGCCCAG | CGGTGCTACG | GAACCGATTA | CTGTGAAGTT | 720
| TGCCAACAAC | CCCAGCCAGA | AGTCCAGCCA | GGCCCTGCTC | TCCCAGCTCT | ACCAGTCCCC | 780

FIGURE 4B

```
TAACCGGCGC TACCCAGGTC CACTTCACCA CCAGGCTCAG AGGTTCAGGC TGGACAATTT    840
GCTTAATATG GCCTATGGCG TAAAGAGACT GATGTCTGGA CCAGTCCCCC CTTCTGCTTG    900
TTCCCCCAGG TTCTCCCCAA TTACCATTGA TGGAATGACA AGCCTTGTGG GAATGAACAT    960
CCCTGGTCAC ACAGGAACTG GGTGGTGCAT CTTTGTCTAC AACCTGTCCC CCGATTCCGA   1020
TGAGAGTGTC CTCTGGCAGC TCTTTGGCCC CTTTGGAGCA GTGAACAACG TAAAGGTGAT   1080
TCGTGACTTC AACACCAACA AGTGCAAGGG ATTCGGCTTT GTCACCATGA CCAACTATGA   1140
TGAGGCGGCC CCAGCCTCAA CGGGTACCGC CGGGAGACA GAGTGTTGCA   1200
AGTTTCCTTT AAAACCAACA AAGCCCACAA GTCCTGAATT TCCCATTCTT ACTTACTAAA   1260
ATATATATAG AAATATATAC GAACAAAACA CACGCGGCA CACACACACA TACACGAAAG   1320
AGAGAGAAAC AAACTTTCA AGGCTTATAT TCAACCATGG ACTTTATAAG CCAGTGTTGC   1380
CTAGTATTAA AACATTGGGT TATCCTGAGG TGTACCAGGA AAGGATTATA ATGCTTAGAA   1440
AAAAAAAAG AAAAAAAAA AACAAAAAA                                      1469
```

ANTIGEN RECOGNIZED BY PATIENTS WITH ANTIBODY ASSOCIATED PARANEOPLASTIC SENSORY NEURONOPATHY, DNA ENCODING SAME AND USES THEREOF

This application is a continuation of U.S. Ser. No. 08/461,027, filed Jun. 5, 1995, now U.S. Pat. No. 5,807,705, issued Sep. 15, 1998, which is a divisional of U.S. Ser. No. 08/210,732, filed Mar. 18, 1994, now U.S. Pat. No. 5,603,934, issued Feb. 18, 1997, which is a continuation of U.S. Ser. No. 07/665,959, filed Mar. 4, 1991, now abandoned, the contents of which are hereby incorporated by reference into the present application.

This invention was made in the course of work under Grant No. PD 359 from the American Cancer Society. The United States government has certain rights in this invention.

BACKGROUND OF THE INVENTION

Throughout this application various references are referred to within parentheses. Disclosures of these publications in their entirety are hereby incorporated by reference into this application to more fully describe the state of the art to which this invention pertains. Full bibliographic citations for these references maybe found at the end of this application, immediately preceding the claims.

Paraneoplastic sensory neuronopathy is a rare remote effect of cancer characterized clinically and pathologically by neuronal loss and inflammatory infiltrates. (1, 6, 7) A high percentage of such patients harbor a characteristic serum antibody which has been called anti-Hu. (4) These sera react with a group of proteins which have been found to be specifically expressed in tumor tissue (usually small cell lung cancer) and brain. (8) This observation suggested a model for the neurological dysfunction in which an immune response primarily directed against a tumor antigen is misdirected against similar antigens expressed in brain. (4,5) The synthesis of the anti-Hu antibody in the brain and the specific deposits of IgG and infiltrating lymphocytes provide circumstantial evidence for this model.

In addition to their neurological interest these cancer patients are unique in that they make a profound immunological response to their tumor. The mechanisms underlying this specific anti-tumor response are not well understood. It is not because these patients uniquely express the Hu-antigen in their small cell lung tumors. All small cell lung tumors (so far analyzed) express the Hu antigen. There are a number of possible mechanisms; (a) the Hu antigen may be mutated and perceived as foreign, (b) in the individuals the expression of a brain protein in extra-neural tissue provokes an extraordinary response, (c) there is an unknown secondary contributing factor e.g., viral infection.

Irrespective of the mechanism involved, the sera of these patients (which contains high-titre anti-Hu IgG) provides a reagent to isolate and characterize human small cell lung cancer tumor antigens.

SUMMARY OF THE INVENTION

An isolated nucleic acid sequence encoding Hu paraneoplastic antigenic polypeptide is provided by this invention. This invention also provides a purified Hu antigenic polypeptide and compositions containing the purified Hu antigenic polypeptide.

A method of detecting an antibody associated with paraneoplastic sensory neuronopathy (PSN) is provided by this invention. This method comprises contacting a suitable sample with the purified Hu antigenic polypeptide labelled with a detectable marker under conditions so as to form a complex between the purified Hu antigenic polypeptide and the antibody, detecting the presence of any complex so formed, thereby detecting an antibody associated with paraneoplastic sensory neuronopathy.

Also provided by this invention is a method of determining whether a patient exhibiting neurological symptoms harbors a tumor expressing Hu antigen, which comprises contacting a suitable tumor sample from the patient, with the monoclonal antibody directed against Hu antigen, the monoclonal antigen being labeled with a detectable marker, under suitable conditions so as to form a complex between the antibody and the tumor antigen, detecting the presence of any complex so formed, the presence of complex being a positive determination that the patient has a tumor which expresses Hu antigen.

A method of inhibiting the proliferation of neoplastic cells in a patient with small cell lung cancer also is provided by this invention. This method comprises administering to the patient an effective amount of a monoclonal antibody directed to the Hu paraneoplastic tumor antigen, the monoclonal antibody being labeled with a therapeutic agent, in an amount which is effective to inhibit the proliferation of the neoplastic cells, thereby inhibiting the proliferation of neoplastic cells in a patient exhibiting paraneoplastic sensory neuronopathy.

This invention further provides a method of imaging neoplastic cells in a patient, wherein the neoplastic cells are associated with paraneoplastic sensory neuronopathy, which comprises administering to the patient an effective amount of a monoclonal antibody directed to Hu paraneoplastic antigen, the monoclonal antibody being labelled with an imaging agent, under conditions to form a complex between the monoclonal antibody and the tumor antigen, imaging any complex so formed, thereby imaging neoplastic cells in a patient.

DETAILED DESCRIPTION OF THE INVENTION

This invention provides an isolated nucleic acid sequence encoding an Hu paraneoplastic antigenic polypeptide. As used herein, the term Hu paraneoplastic antigenic polypeptide encompasses any amino acid sequence having the biological activity of an Hu antigenic protein, i.e., a protein which may specifically form a complex with an antibody which is characteristic of paraneoplastic sensory neuronopathy. This antibody has also been called anti-Hu. This antibody, i.e., anti-Hu, is characteristically found in patients with paraneoplastic sensory neuronopathy, a disorder of the brain found in association with neoplasms of lung.

Figure 4:
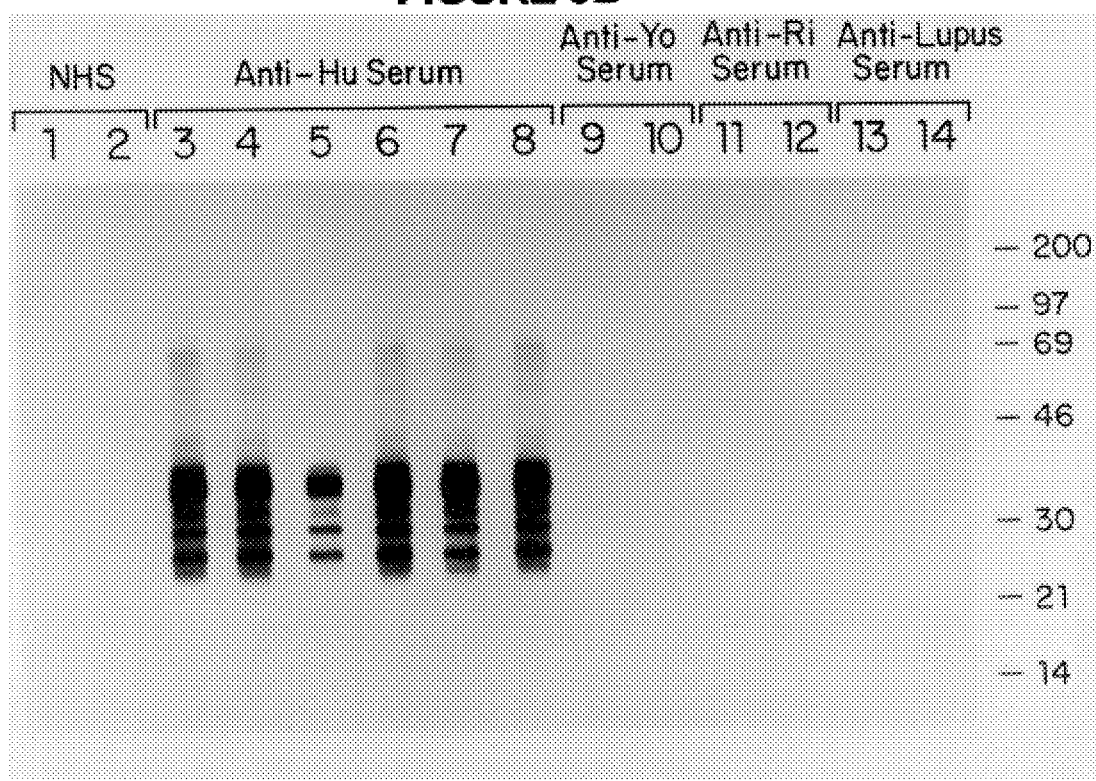
FIGS. 4A and 4B show the nucleotide sequence for cDNA pHB 1.5. (Sequence I.D. No. 1).

In one embodiment of this invention, the isolated nucleic acid sequence described hereinabove is DNA. In other embodiments of this invention, the isolated nucleic acid sequence described hereinabove is cDNA, or it is RNA. In the preferred embodiment of this invention, the isolated nucleic acid sequence is a cDNA sequence as shown in sequence ID No. 1, also FIG. 4.

A vector which comprises the isolated nucleic acid molecule described hereinabove also is provided. Suitable vectors comprise, but are not limited to, a plasmid or a virus. This vector may be transfected into a suitable host cell to form a host vector system for the production of a polypeptide having the biological activity of the Hu antigenic polypeptide.

This invention further provides an isolated DNA or cDNA molecule described hereinabove wherein the host cell is selected from the group consisting of bacteria cells such as *E. coli*, yeast and fungi cells, insect cells and animal cells. Suitable animal cells include, but are not limited to Vero cells, HeLa cells, Cos cells, CV1 cells and primary mouse cells.

Further provided by this invention is a method for producing a polypeptide having the biological activity of the Hu antigenic polypeptide comprising the steps of: a) culturing the host vector system described hereinabove under suitable conditions permitting production of the polypeptide and b) recovering the polypeptide produced. This invention also provides the polypeptide produced by this method.

Throughout this application, references to specific nucleotides are to nucleotides present on the coding strand of the nucleic acid. The following standard abbreviations are used throughout the specification to indicate specific nucleotides:

| C = cytosine | A = adenosine |
|---|---|
| T = thymidine | G = guanosine |
| U = uracil | |

This invention also encompasses DNAs and cDNAs which encode amino acid sequences which differ from those of the Hu paraneoplastic antigenic polypeptide, but which should not produce phenotypic changes. Alternatively, this invention also encompasses DNAs and cDNAs which hybridize to the DNA and cDNA of the subject invention. Hybridization methods are well known to those of ordinary skill in the art. This invention also encompasses cDNA and DNA molecules characterized by changes in non-coding regions that do not alter the phenotype of the polypeptide produced.

Also provided by this invention is a purified, Hu antigenic polypeptide. The purified Hu antigenic polypeptide may be labeled with a detectable marker. For the purposes of this invention, suitable detectable markers include, but are not limited to detectable markers selected from the group consisting of radioisotopes, dyes, enzymes and biotin.

This invention further provides a monoclonal antibody directed to an epitope on the Hu antigenic polypeptide. In one embodiment of this invention, the monoclonal antibody is a mouse monoclonal antibody. In another embodiment of this invention, the monoclonal antibody is a human monoclonal antibody.

For the isolation of mouse monoclonal antibodies, eight week old mice may be injected interperitoneally with about 50 micrograms of a synthetic, purified Hu antigenic polypeptide, (prepared as described above) in complete Freud's adjuvant 1:1 volume. Mice will then be boosted, at monthly intervals, with the polypeptide, mixed with incomplete Freund's adjuvant, and bled through the tail vein. On days 4, 3, and 2 prior to fusion, mice will be boosted intravenously with 50 micrograms of the polypeptide in saline. Splenocytes will then be fused with non-secreting myeloma cells according to procedures which have been described and are known to those of ordinary skill in the art to which this invention pertains. Some time later, approximately two weeks later, hybridoma supernatant will then be screened for binding activity against the Hu antigenic polypeptide as described hereinafter.

Positive clones will then be isolated and propagated. Isolates of human monoclonal antibodies will be similar except β cells will be isolated from patients and transformed with EBV. β cells will then be fused with non-secreting myeloma cells according to procedures which have been described and are known to those of ordinary skill in the art to which this invention pertains. Some time later, approximately two weeks later, hybridoma supernatant will then be screened for binding activity against the Hu antigenic polypeptide as described hereinafter. Positive clones will then be isolated and propagated.

In addition, this invention also provides the monoclonal antibody described hereinabove conjugated to a therapeutic agent. For the purposes of this invention, suitable therapeutic agents include, but are not limited to, a therapeutic agent selected from the group consisting of radioisotopes, toxins, toxoids, and chemotherapeutic agents. Also provided by this invention is the monoclonal antibody described hereinabove conjugated to a detectable marker. Suitable detectable markers include, but are not limited to, enzymes, radioisotopes, dyes and biotin. This invention further provides monoclonal antibodies as described hereinabove conjugated to an imaging agent. Suitable imaging agents include, but are not limited to radioisotopes, such as, $^{32}P$, $^{35}S$, and $^{131}I$. Methods of utilizing the monoclonal antibody conjugated to an imaging agent, to image tumor cells, are well known to those of ordinary skill in the art.

Also provided by this invention are pharmaceutical compositions comprising the purified, Hu antigenic polypeptide described hereinabove alone, or conjugated to any one of the following, a detectable marker, a therapeutic agent, or an imaging agent, as described hereinabove and a pharmaceutically acceptable carrier. Further provided are pharmaceutical compositions comprising the monoclonal antibody described hereinabove alone, or conjugated to any one of the following, a detectable marker, a therapeutic agent, or an imaging agent. As used herein, the term "pharmaceutically acceptable carrier" encompasses any of the standard pharmaceutical carriers, such as phosphate buffered saline solution, water, emulsions, such as a oil/water emulsions, and various types of wetting agents.

A method of detecting an antibody associated with paraneoplastic sensory neuronopathy "PSN", i.e., the Hu antigenic protein, is also provided by this invention. This method comprises contacting a suitable sample with a purified, Hu antigenic polypeptide described hereinabove under conditions so as to form a complex between the purified Hu antigenic polypeptide and the antibody, detecting the presence of any complex so formed, thereby detecting an antibody associated with paraneoplastic sensory neuronopathy. Suitable samples include any sample suspected containing an antibody associated with sensory neuronopathy, such as serum or cerebral-spinal fluid. In one embodiment of the invention the synthetic, purified Hu antigenic polypeptide is labeled with a detectable marker selected from the group consisting of radioisotopes, dyes, enzymes and biotin. For the purposes of this invention, suitable radioisotopes include, but are not limited to, $^{32}$P, $^{35}$S, and $^{131}$I.

Also provided by this invention is a method of determining whether a patient exhibiting neurological symptoms harbors a tumor expressing the Hu antigen, which comprises obtaining the suitable tumor sample from the patient, contacting the suitable tumor sample with a monoclonal antibody directed against the Hu antigen, under conditions so as to form a complex between the antibody and the Hu antigen, detecting the presence of any complex so formed, the presence of a complex being a positive determination that the patient harbors a tumor expressing the Hu antigen. In one embodiment of this invention, the monoclonal antibody is labeled with a detectable marker. For the purposes of this invention, suitable detectable markers include, but are not limited to a detectable marker selected from the group consisting of radioisotopes, dyes, enzymes and biotin. Suitable radioisotopes have been described hereinabove.

Further provided by this invention is a method of inhibiting the proliferation of neoplastic cells in a patient with small cell lung cancer. This method comprises administering to the patient an effective amount of the monoclonal antibody or composition described hereinabove conjugated to a therapeutic agent, in an amount which is effective to inhibit the proliferation of neoplastic cells, and under suitable conditions so as to form a complex between an antigen associated with the neoplasm and the monoclonal antibody, thereby inhibiting the proliferation of neoplastic cells. As used herein, an effective amount is any amount which is effective to inhibit the proliferation of neoplastic cells. As is known to those of ordinary skill in the art, effective amounts vary with the type of therapeutic agent utilized, as well the neoplastic cell tumor being treated. It is well known to those of ordinary skill in the art how to determine an effective amount of a suitable therapeutic agent.

As used herein, "administering" means a method of administering to the patient. Such methods are well known to those skilled in the art and include, but are not limited to administration orally, intravenously, or parenterally. Administration of the agent may be effected continuously or intermittently, such that the amount of the therapeutic agent in the patient is effective to inhibit proliferation of neoplastic cells. For the purposes of this invention suitable therapeutic agents include radioisotopes, toxins, toxoids, and chemotherapeutic agents.

Also provided by this invention is a method of imaging neoplastic cells in a patient, wherein the neoplastic cells are associated with paraneoplastic sensory neuronopathy.

The method comprises administering to the patient the monoclonal antibody described hereinabove which is labelled with an imaging agent, for example $^{131}$I, or a composition containing the same, and administered it to the patient to bind to a Hu antigen present on or within the neoplastic cells so as to form a complex between the monoclonal antibody and the antigen, detecting any complex so formed, thereby imaging neoplastic cells in a patient having neoplastic cells expressing Hu antigen. As is well known to those of ordinary skill in the art, a suitable amount of monoclonal antibody or composition is any amount which is effective to image the neoplastic cells, for example, from about 0.1 mCi to about 50.0 mCi. In addition, an effective amount of the monoclonal antibody may be an amount from about 0.01 mg to about 100 mg. Suitable methods of administering the imaging agent are as described hereinabove.

Imaging of any complex so formed may be carried out using single photon computed emission tomography (SPECT) or by using a gamma camera.

This invention provides a method to isolate and clone specific anti-tumor antigen human monoclonal antibodies. The β lymphocytes will be isolated from patient's blood, transformed with E.B.V. (Epstein Barr Virus) and selected by the specific recognition of the recombinant Hu antigen.

This invention also provides a method to isolate and clone specific anti-tumor T cells. The T cells will be isolated from patient's blood, stimulated to grow with interleukin 2 and selected by specific recognition of the recombinant Hu antigen.

Further provided by this invention is a diagnostic method useful for predicting small cell lung cancer in patients. This method comprises contacting a suitable sample, such as serum from the patient with a labelled antigenic polypeptide of this invention under suitable conditions so as to form a complex between the antigenic polypeptide and any antibody in the sample, detecting the presence of any complex so formed, the presence of complex being predictive of small cell lung cancer.

Materials and Methods

Materials

Sera from patients with antibody-associated paraneoplastic sensory neuropathy was obtained from physicians. A cerebellar λ ZAP expression library was obtained from Stratagene™.

Methods

Screening of λ Cerebellar Expression Library

Recombinant phage were screened at a density of 2×10$^4$ pfu per 150 mm plate of *E. coli* XLI-Blue. After incubation for 6 hours at 37° C., the plates were overlaid with filters soaked in 1PTG (10 mM) and incubated for a further 12 hours at 37° C. The filters were then removed and incubated with anti Hu sera (2 μg/ml IgG), for 2 hours at room temperature. The filters were then washed with TBST (50 mM Tris (pH 7.4), 100 mM NaCl, 0.2% Triton) and incubated with I$^{125}$ Protein A. After washing with TBST the filters were exposed to XRA5 film at −70° C. Clones yielding positive signals were purified by several rounds of antibody screening until 100% of the plaques gave positive signals.

Analysis of Fusion Proteins

Phage clones were subcloned into p Bluescript (pBs) using the phage rescue protocol. [10] Individual clones were grown to an optical density of 0.6 and induced by adding IPTG (10 mM). After 1 hour of induction at 37° C., the bacterial cells were isolated by centrifugation resuspended in lysis buffer (2% SDS, 50 mM Tris (pH 6.8)). Lysates were then resolved by 8% polyacrylamide SDS gel electrophoresis and transferred to nitrocellulose [11]. The filters were then incubated with anti-Hu sera (5 μg/ml in TBST) for 2 hours at room temperature. The filters were then washed with TBST and incubated with I$^{125}$ protein A (0.1 μCi/ml).

After a further washing with TBST, the filters were exposed to XRA5 film at −70° C.

DNA Sequence Analysis

All sequencing was based on the dideoxy termination method [10]. Double strand DNA was sequenced on both strands using SK, KS, M13 universal and reverse primers, and internal oligonucleotide primers. Sequences were merged and analyzed for open reading frame and functional motifs with the Macvector analysis software.

Results

Isolation of Positive λ Clones

Figure 1:
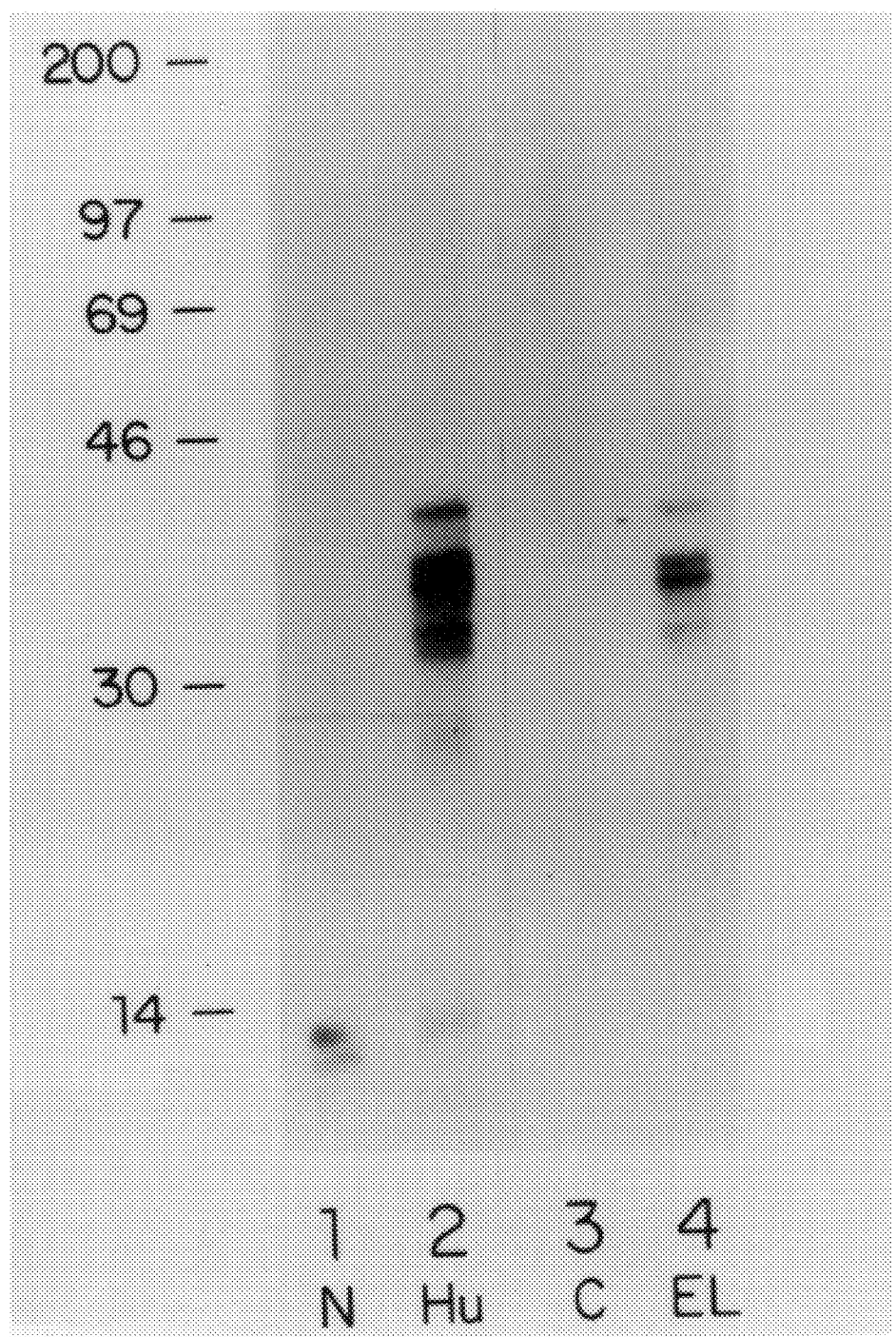
FIG. 1 shows the typical Hu antigen identified in Western Blot analysis of human cortical neurons and the epitope analysis.

Screening of the cerebellar cell λ ZAP expression library with a typical high-titer anti-Hu sera resulted in the isolation of 8 positive clones. None of the clones we recognized by normal human sera. The clones were characterized by insert size and similarity (by Southern blot hybridization) to each other. Clones HB 1.5 and HB 0.8 belong to one gene product. The relationship between the human cerebral antigen Hu and the fusion protein encoded by clones HB 1.5 and HB 0.8 was examined by the epitope selection method. In this procedure the antibodies that recognize the recombinant fusion protein are isolated and reacted with a Western blot of the tissue antigen. Purified antibodies from bona-fide clones should identify the original antigen of interest. FIG. 1 (lane 2) shows the typical Hu antigen identified in western blot analysis of human cortical neurons. Normal human serum only identifies a non-specific antigen of 12 kb in wt. FIG. 1 (lane 4) shows that affinity purified antibodies selected by reactivity with the fusion proteins encoded by clones HB 1.5 recognized the Hu-antigen expressed in human cortical neurons. A mock purification of anti-Hu sera employing an irrelevant fusion protein served as the negative control (FIG. 1, lane 3). It was therefore concluded that the gene product encoded by clones HB 1.5 and HB 0.8 was related to the Hu-antigen.

Figure 2:
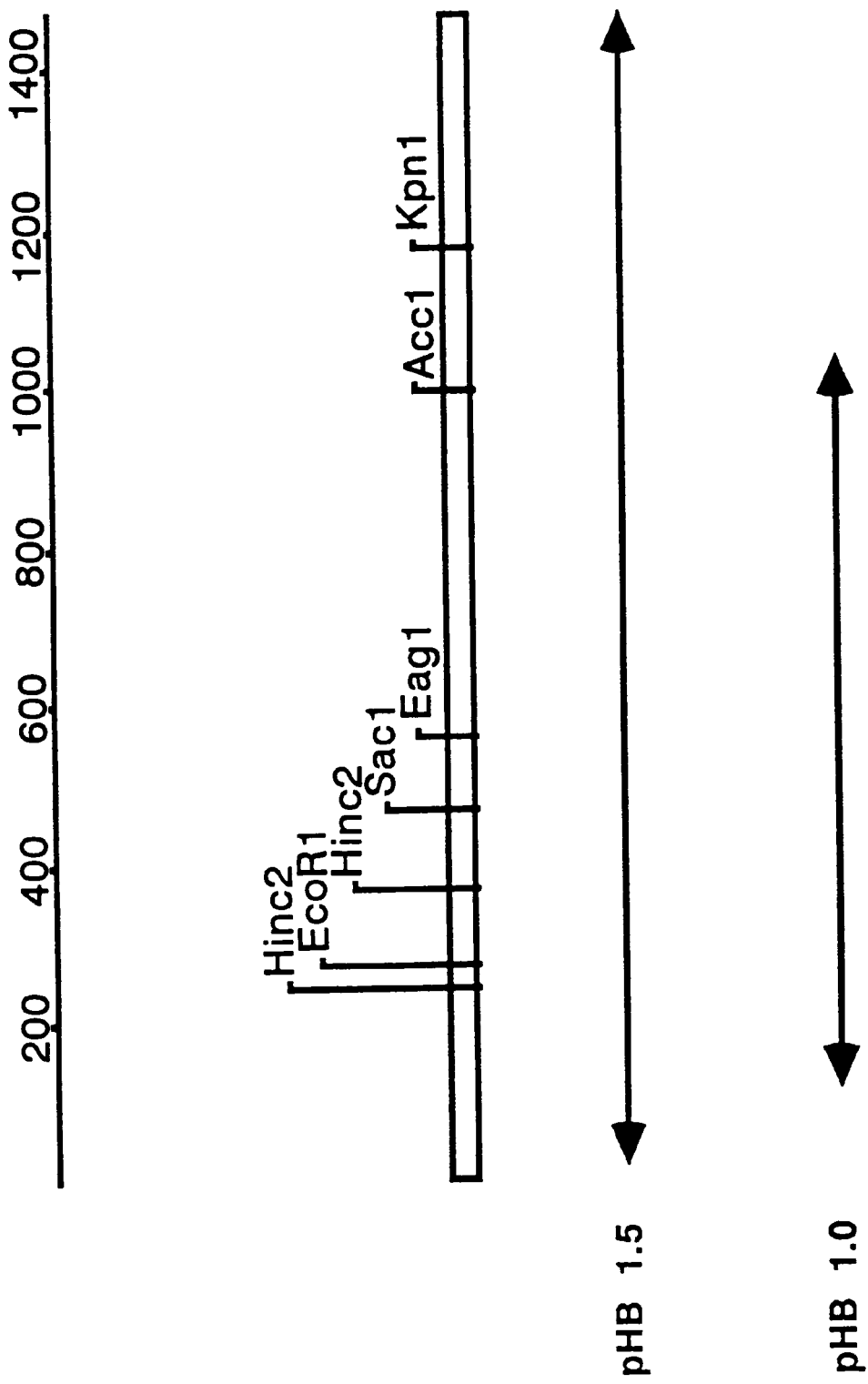
FIG. 2 shows restriction enzyme map of clone pHB 1.5 and clone pHB 1.0.

Both λ phage clones were then subcloned into PBS utilizing the phagemid rescue procedure. The resulting bacterial plasmids pHB 1.5 and pHB 0.8 had inserts of 1.5 kb and 0.8 kb, respectively. Restriction enzyme digestion confirmed that the two clones were related and a simplified map is shown in FIG. 2.

Specific Recognition of cDNA Clones by Anti-Hu Sera

Figure 3:
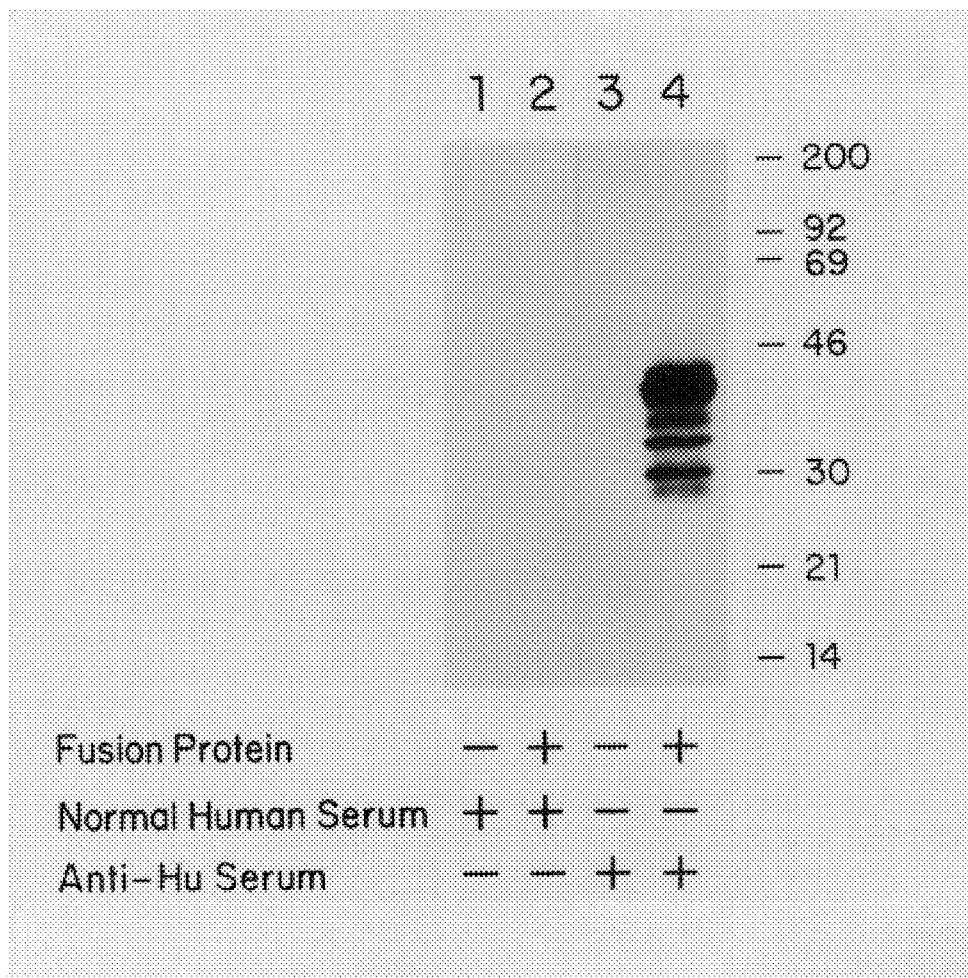
FIGS. 3A and 3B show the Western Blot analysis of the fusion protein encoded by pHB 1.5.

The reactivity of anti-Hu sera and various negative control sera was established by Western blot analysis of the fusion protein encoded by pHB 1.5. Anti-Hu sera identify a fusion protein of 55 kd in extracts of pHB 1.5 (FIG. 3A, lane 4). No reactivity was observed with extracts of PBS (the parental plasmid vector with no insert) (FIG. 3A, lane 3). No reaction of the pHB 1.5 fusion protein was observed with normal human serum (FIG. 3A, lane 3). The minor bands visible in FIG. 3A (lane 4) correspond to proteolytic fragments of the 55 kd fusion protein. FIG. 3B shows that reactivity with sera previously characterized as anti-Hu were positive (lanes 3–8). Negative controls included: normal human sera (lanes 1 and 2), sera from patients with antibody-associated paraneoplastic cerebellar degeneration (anti-yo), serum from another antibody-associated paraneoplastic syndrome (anti-Ri), and lupus serum. In total, all fifty available anti-Hu sera were positive and no reactivity was detected with a total of 150 negative sera. It was therefore concluded that the reactivity of serum with the pHB 1.5 fusion protein is a reliable assay for antibody-associated paraneoplastic sensory neuronopathy (anti-Hu syndrome).

Histochemical Identification Of Lymphocytes That Recognize the Hu antigen

The brain and small cell lung cancer of patients suffering from the anti-Hu syndrome contain infiltrating lymphocytes. In order to establish whether the infiltrating lymphocytes are directed against the Hu antigen, the fusion protein encoded pHB 1.5 was purified by preparative gel electrophoresis and labelled with biotin. Protein eluted from the sera region of a preparative gel containing E. coli extract was also biotinylated and served as a negative control. Biotinylated recombinant Hu-antigen and irrelevant E. coli protein were then incubated with frozen sections of brain and small cell lung cancer tissue from an anti-Hu patient. Bound protein was then visualized by incubation with avidin biotin peroxidase complex and DAB. Biotinylated HuD antigen reacted specifically with lymphocytes in the small cell lung cancer and brain of an affected individual. There was no reactivity with normal human brain. The irrelevant E. coli protein did not specifically react with any cell line in any of the tissues. Examination of the stained lymphocytes revealed them to be both B and T cells.

Sequence Analysis of pHB 1.5 and pHB 0.8 pHB 1.5 and pHB 0.8 use sequenced completely on both strands (FIG. 2). There is a poly (A) tail at the 3' end of pHB 1.5. A long open reading frame encoding a predicted bas c (P.I.=9.5) protein of 380 amino acids (M.Wt=41 kd) was found starting with an ATG at position 95 and terminating with a codon at position 1234. The open reading frame is preceded by three in frame termination codons at positions 5, 8, and 17 indicating that the ATG at 95 which satisfies the Kozak consensus rule is probably the true initiating ATG. Examination of the rare codon usage also indicated that the sequences preceding the ATG at 95 do not code for protein. The protein encoded by pHB 1.5 is not in frame with the β galactoside AUG.

Figure 5:
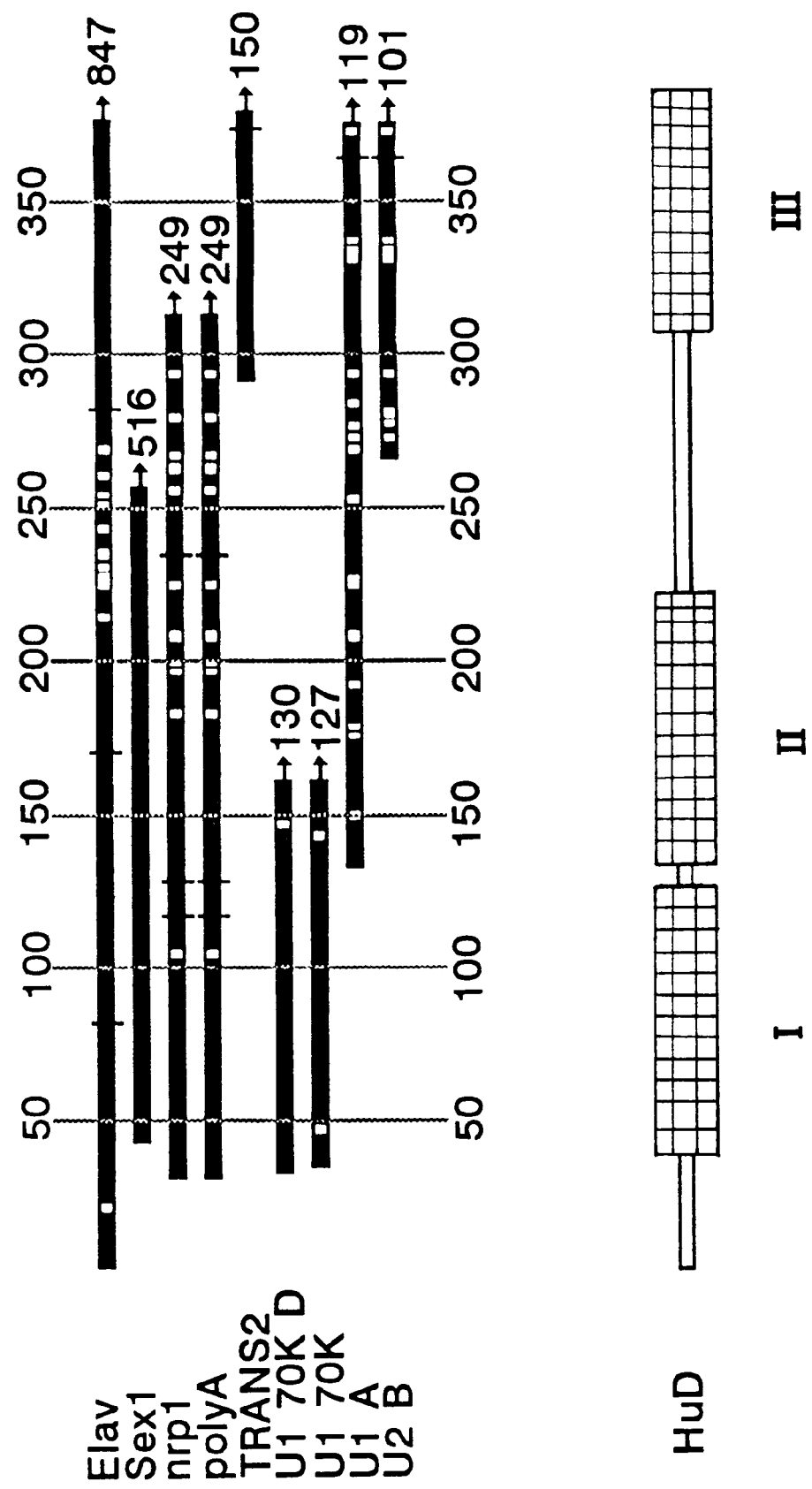
FIG. 5 shows the result of a homology search conducted in data bases. Striking homology was revealed with the drosophila proteins elav and sex lethal.

The predicted amino acid sequence of HuD was used in a homology search of data bases and revealed striking homology with the drosophila protein elav and sex lethal. (FIG. 5A and 5B).

References

1. Henson, R. and Urich, H. "Cancer and the nervous system." 1982 Blackwell Scientific. Oxford.
2. Graus, F., Cordon-Cardo, C. and Posner, J. Neuronal antinuclear antibody in sensory neuronopathy from lung cancer. Neurology 35:538–543, 1985.
3. Dalmau, J., Furneaux, M. M., Gralla, R. J., Kris, M. G., Posner, J. B. Detection of the anti-Hu antibody in the serum of patients with small cell lung cancer-a quantitative western blot analysis. Ann. Neurol 27:544–552, 1990.
4. Furneaux, H., Reich, L. and Posner, J. Central nervous system synthesis of autoantibodies in paraneoplastic syndromes. Neurology. 40: 1085–1091, 1990.
5. Dalmau, J. et al. Immunological Study of Central Nervous System and Tumor in Tumor Paraneoplastic Encephalomyelitis/Sensory Neuronopathy Associated With Small Lung Cancer, Ann. of Neur., submitted for publication.
6. Brain, L. and Wilkinson, M. 88: 465–478, 1965.
7. Furneaux, H. and Posner, J. Paraneoplastic neurological syndromes. Proc. Assoc. Res. Nerv. Men. Dis. 68: 187–219, 1990.

What is claimed is:

1. A method of detecting an antibody associated with paraneoplastic sensory neuronopathy in a patient sample, comprising contacting the sample with a purified Hu antigenic polypeptide under conditions effective to form a complex between the purified Hu antigenic polypeptide and the antibody, detecting the presence of any complex so formed, thereby detecting the antibody associated with paraneoplastic sensory neuronopathy.

2. The method of claim 1, wherein the purified Hu antigenic polypeptide is labelled with a detectable marker.

3. The method of claim 2, wherein the detectable marker is selected from the group consisting of a radioisotope, a dye, an enzyme and biotin.

4. A method of determining whether a patient exhibiting neurological symptoms harbors a tumor expressing Hu antigen, comprising contacting a sample from the patient with an antibody directed to an epitope on a purified Hu antigenic polypeptide.

5. The method of claim 4, wherein the antibody is labelled with a detectable marker.

6. The method of claim 5, wherein the detectable marker is selected from the group consisting of a radioisotope, a dye, an enzyme and biotin.

7. A method of inhibiting the proliferation of neoplastic cells in a patient having paraneoplastic sensory neuronopathy which comprises administering to the patient an effective amount of of an antibody directed to an epitope on purified Hu antigenic polypeptide, wherein the antibody is conjugated to a therapeutic agent, effective to inhibit the proliferation of neoplastic cells in the patient having paraneoplastic sensory neuronopathy.

8. A method of claim 7, wherein the therapeutic agent is a radioisotope, toxin, toxoid or chemotherapeutic agent.

9. The method of claim 1, wherein said Hu polypeptide is purified by gel electrophoresis.

10. The method of claim 9, wherein said gel electrophoresis is carried out on brain tissue containing Hu polypeptide.

11. The method of claim 1, wherein said patient sample is a blood sample.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 1469 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: cDNA encoding Hu antigenic protein (vii) IMMEDIATE SOURCE:
      (B) CLONE: pHB 1.5

(x) PUBLICATION INFORMATION:
      (A) AUTHORS: Furneaux, Henry M.
      (C) JOURNAL: Cell (xi) SEQUENCE DESCRIPTION: SEQ ID NO:1:

```
CCAATAGTAG TCATTTTAAA TATATATTCT GAAATCTTTG CAAATTTTAA CAGAAGAGTC      60
GAAGCTCTGC GAGACCCAAT ATTTGCCAAT AAGAATGGTT ATGATAATTA GCACCATGGA     120
GCCTCAGGTG TCAAATGGTC CGACATCCAA TACAAGCAAT GGACCCTCCA GCAACAACAG     180
AAACTGTCCT TCTCCCATGC AAACAGGGGC AACCACAGAT GACAGCAAAA CCAACCTCAT     240
CGTCAACTAT TTACCCCAGA ATATGACCCA AGAAGAATTC AGGAGTCTCT TCGGGAGCAT     300
TGGTGAAATA GAATCCTGCA AACTTGTGAG AGACAAAATT ACAGGACAGA GTTTAGGGTA     360
TGGATTTGTT AACTATATTG ATCCAAAGGA TGCAGAGAAA GCCATCAACA CTTTAAATGG     420
ACTCAGACTC CAGACCAAAA CCATAAAGGT CTCATATGCC CGTCCGAGCT CTGCCTCAAT     480
CAGGGATGCT AACCTCTATG TTAGCGGCCT TCCCAAAACC ATGACCCAGA AGGAACTGGA     540
GCAACTTTTC TCGCAATACG GCCGTATCAT CACCTCACGA ATCCTGGTTG ATCAAGTCAC     600
AGGAGTGTCC AGAGGGGTGG GATTCATCCG CTTTGATAAG AGGATTGAGG CAGAAGAAGC     660
CATCAAAGGG CTGAATGGCC AGAAGCCCAG CGGTGCTACG GAACCGATTA CTGTGAAGTT     720
TGCCAACAAC CCCAGCCAGA AGTCCAGCCA GGCCCTGCTC TCCCAGCTCT ACCAGTCCCC     780
TAACCGGCGC TACCCAGGTC CACTTCACCA CCAGGCTCAG AGGTTCAGGC TGGACAATTT     840
GCTTAATATG GCCTATGGCG TAAAGAGACT GATGTCTGGA CCAGTCCCCC CTTCTGCTTG     900
TTCCCCCAGG TTCTCCCCAA TTACCATTGA TGGAATGACA AGCCTTGTGG GAATGAACAT     960
CCCTGGTCAC ACAGGAACTG GGTGGTGCAT CTTTGTCTAC AACCTGTCCC CCGATTCCGA    1020
TGAGAGTGTC CTCTGGCAGC TCTTTGGCCC CTTTGGAGCA GTGAACAACG TAAAGGTGAT    1080
TCGTGACTTC AACACCAACA AGTGCAAGGG ATTCGGCTTT GTCACCATGA CCAACTATGA    1140
TGAGGCGGCC ATGGCCATCG CCAGCCTCAA CGGGTACCGC CTGGGAGACA GAGTGTTGCA    1200
AGTTTCCTTT AAAACCAACA AAGCCCACAC GTCCTGAATT TCCCATTCTT ACTTACTAAA    1260
ATATATATAG AAATATATAC GAACAAAACA CACGCGCGCA CACACACACA TACACGAAAG    1320
AGAGAGAAAC AAACTTTTCA AGGCTTATAT TCAACCATGG ACTTTATAAG CCAGTGTTGC    1380
```

-continued

```
CTAGTATTAA AACATTGGGT TATCCTGAGG TGTACCAGGA AAGGATTATA ATGCTTAGAA      1440

AAAAAAAAAG AAAAAAAAAA AACAAAAAA                                       1469
```